US008639002B2

(12) United States Patent
Tanaka et al.

(10) Patent No.: US 8,639,002 B2
(45) Date of Patent: Jan. 28, 2014

(54) MEDICAL IMAGE PROCESSING APPARATUS AND METHOD FOR CONTROLLING MEDICAL IMAGE PROCESSING APPARATUS

(75) Inventors: Kenichi Tanaka, Hino (JP); Hirokazu Nishimura, Hachioji (JP); Sawako Shibata, Tama (JP); Tetsuo Nonami, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/591,289

(22) Filed: Aug. 22, 2012

(65) Prior Publication Data

US 2013/0051641 A1 Feb. 28, 2013

Related U.S. Application Data

(63) Continuation of application No. PCT/JP2011/078141, filed on Dec. 6, 2011.

(30) Foreign Application Priority Data

Feb. 22, 2011 (JP) ................................. 2011-036168

(51) Int. Cl.
 *G06K 9/00* (2006.01)
 *G06K 9/48* (2006.01)
(52) U.S. Cl.
 USPC .......................................... 382/128; 382/199
(58) Field of Classification Search
 None
 See application file for complete search history.

(56) References Cited

U.S. PATENT DOCUMENTS

| 2003/0071894 | A1 | 4/2003 | Higuchi et al. | |
|---|---|---|---|---|
| 2003/0179915 | A1* | 9/2003 | Goto | 382/128 |
| 2004/0197015 | A1* | 10/2004 | Fan et al. | 382/128 |
| 2009/0208071 | A1* | 8/2009 | Nishimura et al. | 382/128 |
| 2011/0299748 | A1* | 12/2011 | Nishimura et al. | 382/128 |
| 2012/0027275 | A1* | 2/2012 | Fleming | 382/128 |

(Continued)

FOREIGN PATENT DOCUMENTS

| JP | 2003-93342 A | 4/2003 |
|---|---|---|
| JP | 2005-157902 A | 6/2005 |

OTHER PUBLICATIONS

International Search Report dated Feb. 28, 2012 issued in PCT/JP2011/078141.

(Continued)

*Primary Examiner* — Stephen R Koziol
*Assistant Examiner* — Jonathan S Lee
(74) *Attorney, Agent, or Firm* — Scully, Scott, Murphy & Presser, P.C.

(57) ABSTRACT

A medical image processing apparatus includes a selection portion that selects a pixel of interest from an image composed of a plurality of pixels and obtained by picking up an image of a living tissue, a first feature value calculation portion that calculates a first feature value on the basis of color tone of the pixel of interest and color tones of surrounding pixels, a second feature value calculation portion that calculates a second feature value on the basis of the color tone of the pixel of interest and the color tones of surrounding pixels, an evaluation value calculation portion that calculates an evaluation value on the basis of the first feature value and the second feature value, and an evaluation value judgment portion that judges whether the pixel of interest is a pixel constituting the linear structure, on the basis of the evaluation value.

18 Claims, 4 Drawing Sheets

(56) References Cited

U.S. PATENT DOCUMENTS

2012/0051606 A1* 3/2012 Saikia ............................ 382/128
2012/0121144 A1* 5/2012 Tanaka .......................... 382/128
2012/0177259 A1* 7/2012 Hirota et al. ................... 382/128
2013/0064436 A1* 3/2013 Tanaka et al. .................. 382/128

OTHER PUBLICATIONS

Frangi, A.F., et al., "Multiscale Vessel Enhancement Filtering", Medical Image Computing and Computer-Assisted Intervention, MICCAI '98, vol. 1496, pp. 130-137, (1998).

Nakagawa, T., et al., "Recognition of Optic Nerve Head Using Blood-Vessel-Erased Image and Its Application to Production of Simulated Stereogram in Computer-Aided Diagnosis System for Retinal Images", IEICE Transactions on Information and Systems, D, vol. J89-D, No. 11, pp. 2491-2501, (2006).

Kenshi, Yao, et al., "Diagnosis of Presence and Boundary Early Gastric Cancer with Microvascular Architecture", Endoscoptiva Digestiva, vol. 17, No. 12, pp. 2093-2100, Dec. 2005, together with an English language translation.

* cited by examiner

BLOOD VESSEL
(CONVEX DOWNWARD)

MEDICAL IMAGE PROCESSING APPARATUS AND METHOD FOR CONTROLLING MEDICAL IMAGE PROCESSING APPARATUS

CROSS REFERENCE TO RELATED APPLICATION

This application is a continuation application of PCT/JP2011/078141 filed on Dec. 6, 2011 and claims benefit of Japanese Application No. 2011-036168 filed in Japan on Feb. 22, 2011, the entire contents of which are incorporated herein by this reference.

BACKGROUND OF THE INVENTION

1. Field of the Invention

The present invention relates to a medical image processing apparatus and a method for controlling the medical image processing apparatus and, more particularly, to a medical image processing apparatus for performing processing on a picked-up image of a living tissue inside a body cavity and a method for controlling the medical image processing apparatus.

2. Description of the Related Art

Endoscope systems configured to include an endoscope, a medical image processing apparatus, and the like have been widely used. More specifically, an endoscope system is configured to include, for example, an endoscope which is composed of an insertion portion to be inserted into a body cavity of a subject, an objective optical system arranged at a distal end portion of the insertion portion, and an image pickup portion that picks up an image of an object inside the body cavity formed by the objective optical system and outputs the image as image pickup signals and a medical image processing apparatus that performs processing for displaying the image of the object on a monitor or the like as a display portion on the basis of the image pickup signals. The endoscope system with the above-described configuration enables various findings by observing, for example, mucosal color tone, shape of a lesion, a microstructure on a mucosal surface, and the like in a digestive tract mucosa of a stomach or the like.

Studies on a technology called CAD (computer aided diagnosis or computer aided detection) as in, for example, Kenshi Yao et al., "Sokiigan no bisyokekkankochikuzo niyoru sonzai oyobi kyokaishindan (Diagnosis of Presence and Demarcations of Early Gastric Cancers Using Microvascular Patterns)," Endoscopia Digestiva, Vol. 17, No. 12, pp. 2093-2100, 2005, have been in progress in recent years. The technology enables finding and diagnosing a lesion by extracting, at a mucosal epithelium inside a body cavity, a region where a microvascular structure or a pit (gland opening) structure exists on the basis of image data obtained through pickup of an image of an object by an endoscope or the like and presenting a result of extracting the region.

Additionally, a technique for extracting a blood vessel candidate region as a region where a blood vessel may exist on the basis of image data obtained through pickup of an image of an object by an endoscope or the like and obtaining a result of detecting a blood vessel region as a region where a blood vessel can be regarded as actually existing by performing correction processing such as region expansion or reduction on a result of extracting the blood vessel candidate region is disclosed in, for example, Toshiaki Nakagawa et al., "Recognition of Optic Nerve Head Using Blood-Vessel-Erased Image and Its Application to Simulated Stereogram in Computer-Aided Diagnosis System for Retinal Images," IEICE Trans. D, Vol. J89-D, No. 11, pp. 2491-2501, 2006.

Hemoglobin in erythrocyte has strong absorption characteristics in a band of G (green) light among bands of wavelengths constituting RGB light. For the reason, a density value of G (green) in a region where a blood vessel exists tends to be lower than a density value of G (green) in a region where no blood vessel exists in, for example, image data obtained when an object including the blood vessel is irradiated with RGB light. For example, as a technique which takes the tendency into account, a technique is known for extracting a blood vessel candidate region by applying a band-pass filter to image data obtained through pickup of an image of an object by an endoscope or the like.

SUMMARY OF THE INVENTION

A medical image processing apparatus according to one aspect of the present invention is a medical image processing apparatus for detecting a region where a linear structure exists from a piece of image information that is composed of a plurality of pixels and is obtained by picking up an image of a living tissue, the medical image processing apparatus including: a selection portion that selects a pixel of interest from the piece of image information; a first feature value calculation portion that calculates a first feature value of the pixel of interest that is calculated by a first calculation method for extracting a first feature from the plurality of pixels, on the basis of a piece of color tone information of the pixel of interest and pieces of color tone information of surrounding pixels; a second feature value calculation portion that calculates a second feature value of the pixel of interest that is calculated by a second calculation method different from the first calculation method for extracting a second feature different from the first feature from the plurality of pixels, on the basis of the piece of color tone information of the pixel of interest and pieces of color tone information of surrounding pixels; an evaluation value calculation portion that calculates an evaluation value of the pixel of interest serving as a value used to judge on the basis of the first feature value and the second feature value whether the pixel of interest is a pixel corresponding to the linear structure; and an evaluation value judgment portion that judges whether the pixel of interest is a pixel constituting a linear structure, on the basis of the evaluation value calculated by the evaluation value calculation portion.

A method for controlling a medical image processing apparatus according to one aspect of the present invention is a method for controlling a medical image processing apparatus for detecting pixels in a region where a linear structure exists from a piece of image information that is composed of a plurality of pixels and is obtained by picking up an image of a living tissue, the method for controlling the medical image processing apparatus, including: a selection step of selecting, by the medical image processing apparatus, a pixel of interest from the piece of image information; a first feature value calculation step of calculating, by the medical image processing apparatus, a first feature value of the pixel of interest that is calculated by a first calculation method for extracting a first feature from the plurality of pixels, on the basis of a piece of color tone information of the pixel of interest and pieces of color tone information of surrounding pixels; a second feature value calculation step of calculating, by the medical image processing apparatus, a second feature value of the pixel of interest that is calculated by a second calculation method different from the first calculation method for extracting a second feature different from the first feature from the plurality of pixels, on the basis of the piece of color tone information of the pixel of interest and pieces of color tone information of surrounding pixels; an evaluation value calculation step of calculating, by the medical image processing apparatus, an evaluation value of the pixel of interest serving as a value used to judge on the basis of the first feature value and the second feature value whether the pixel of interest is a pixel corresponding to the linear structure; and an evaluation value judgment step of judging, by the medical image processing apparatus, whether the pixel of interest is a pixel constituting a linear structure, on the basis of the evaluation value calculated in the evaluation value calculation step.

DETAILED DESCRIPTION OF THE PREFERRED EMBODIMENT

An embodiment of the present invention will be described below with reference to the drawings. FIGS. 1 to 6 relate to an example of the present invention.

Figure 1:
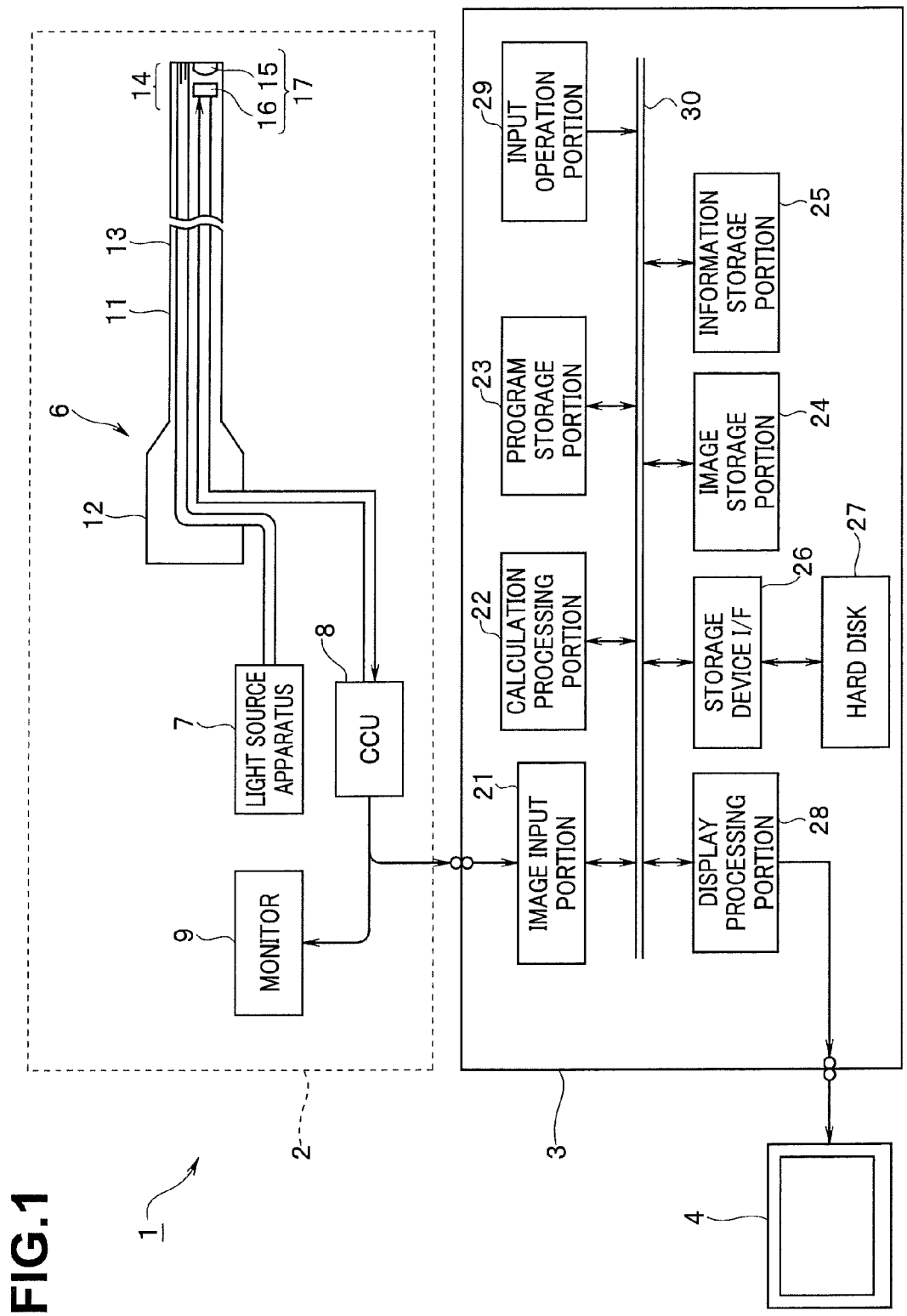
FIG. 1 is a diagram showing a configuration of a main portion of a medical system including a medical image processing apparatus according to an example of the present invention.

FIG. 1 is a diagram showing a configuration of a main portion of a medical system including a medical image processing apparatus according to the example of the present invention.

As shown in FIG. 1, a medical system 1 is configured to include a medical observation apparatus 2 which picks up an image of a living tissue as an object inside a body cavity and outputs a video signal, a medical image processing apparatus 3 which is composed of a personal computer or the like and performs image processing on a video signal outputted from the medical observation apparatus 2 and outputs the video signal after the image processing as an image signal, and a monitor 4 which displays an image based on the image signal outputted from the medical image processing apparatus 3.

The medical observation apparatus 2 is configured to include an endoscope 6 which is inserted into a body cavity, picks up an image of an object inside the body cavity, and outputs the image as an image pickup signal, a light source apparatus 7 which supplies illuminating light (e.g., RGB light) for illuminating the object, the image of which is to be picked up by the endoscope 6, a camera control unit (hereinafter abbreviated as CCU) 8 which performs various types of control on the endoscope 6 and generates and outputs a video signal by subjecting the image pickup signal outputted from the endoscope 6 to signal processing, and a monitor 9 which displays the image of the object picked up by the endoscope 6 on the basis of the video signal outputted from the CCU 8.

The endoscope 6 as a medical image pickup apparatus is configured to include an insertion portion 11 which is to be inserted into a body cavity and an operation portion 12 which is provided on a proximal end side of the insertion portion 11. A light guide 13 for transmitting illuminating light supplied from the light source apparatus 7 is inserted through the insertion portion 11 from the proximal end side of the insertion portion 11 to a distal end portion 14 on a distal end side.

In the light guide 13, a distal end side is arranged at the distal end portion 14 of the endoscope 6, and a rear end side is configured to be connectable to the light source apparatus 7. With the configuration, illuminating light supplied from the light source apparatus 7 is transmitted by the light guide 13 and then exits through an illuminating window (not shown) which is provided in a distal end face of the distal end portion 14 of the insertion portion 11. A living tissue or the like as an object is illuminated with illuminating light exiting through the illuminating window.

An image pickup portion 17 including an objective optical system 16 which is attached to an observation window (not shown) arranged at a position adjacent to the illuminating window and an image pickup device 15 which is arranged at an image formation position of the objective optical system 16 and is composed of a CCD or the like is provided at the distal end portion 14 of the endoscope 6.

The image pickup device 15 is connected to the CCU 8 via a signal line. The image pickup device 15 is driven on the basis of a drive signal outputted from the CCU 8 and outputs an image pickup signal obtained by picking up an image of an object formed by the objective optical system 16 to the CCU 8.

An image pickup signal inputted to the CCU 8 is subjected to signal processing in a signal processing circuit (not shown) which is provided inside the CCU 8, is converted to a video signal, and is outputted. The video signal outputted from the CCU 8 is inputted to the monitor 9 and the medical image processing apparatus 3. With the operations, an image of an object based on the video signal outputted from the CCU 8 is displayed on the monitor 9.

The medical image processing apparatus 3 includes an image input portion 21 which subjects a video signal outputted from the medical observation apparatus 2 to processing such as A/D conversion and generates image data, a calculation processing portion 22 which is configured to include a CPU or the like and performs various types of processing on image data and the like outputted from the image input portion 21, a program storage portion 23 which stores, e.g., a program (and software) related to processing to be performed in the calculation processing portion 22, an image storage portion 24 which can store image data and the like outputted from the image input portion 21, and an information storage portion 25 which can temporarily store a processing result from the calculation processing portion 22.

The medical image processing apparatus 3 also includes a storage device interface 26 which is connected to a data bus 30 (to be described later), a hard disk 27 which can retain a processing result from the calculation processing portion 22 that is outputted via the storage device interface 26, a display processing portion 28 which generates image signals for displaying as an image a processing result from the calculation processing portion 22 and the like on the monitor 4 and outputs the image signals, and an input operation portion 29 which is configured to include an input device such as a keyboard and can input a parameter in processing by the calculation processing portion 22, operation instructions to the medical image processing apparatus 3, and the like.

Note that the image input portion 21, the calculation processing portion 22, the program storage portion 23, the image storage portion 24, the information storage portion 25, the storage device interface 26, the display processing portion 28, and the input operation portion 29 of the medical image processing apparatus 3 are connected to one another via the data bus 30.

Figure 2:
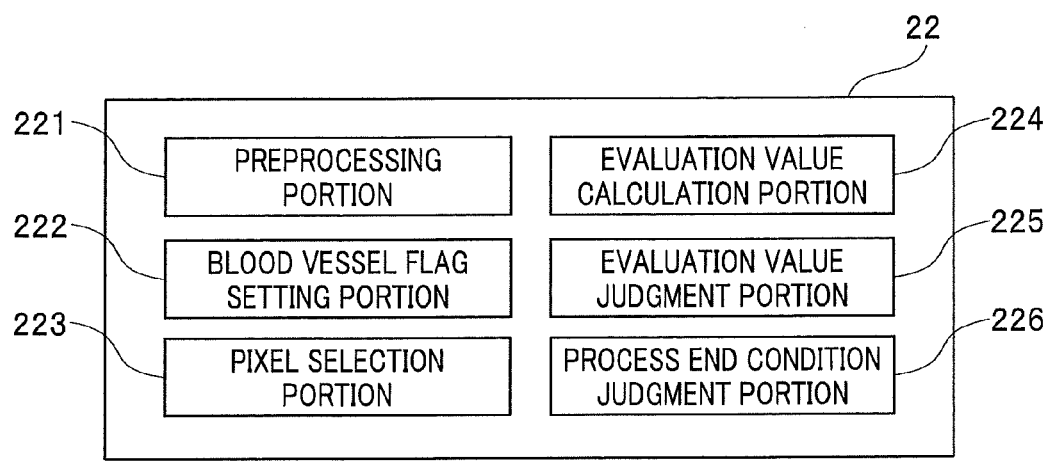
FIG. 2 is a diagram showing an example of a configuration of a calculation processing portion of the medical image processing apparatus according to the present example.

FIG. 2 is a diagram showing an example of a configuration of the calculation processing portion of the medical image processing apparatus according to the present example.

As shown in FIG. 2, the calculation processing portion 22 is configured to include a preprocessing portion 221, a blood vessel flag setting portion 222, a pixel selection portion 223, an evaluation value calculation portion 224, an evaluation value judgment portion 225, and a process end condition judgment portion 226 corresponding to functions which are implemented by execution of a program, software, or the like stored in the program storage portion 23.

Figure 3:
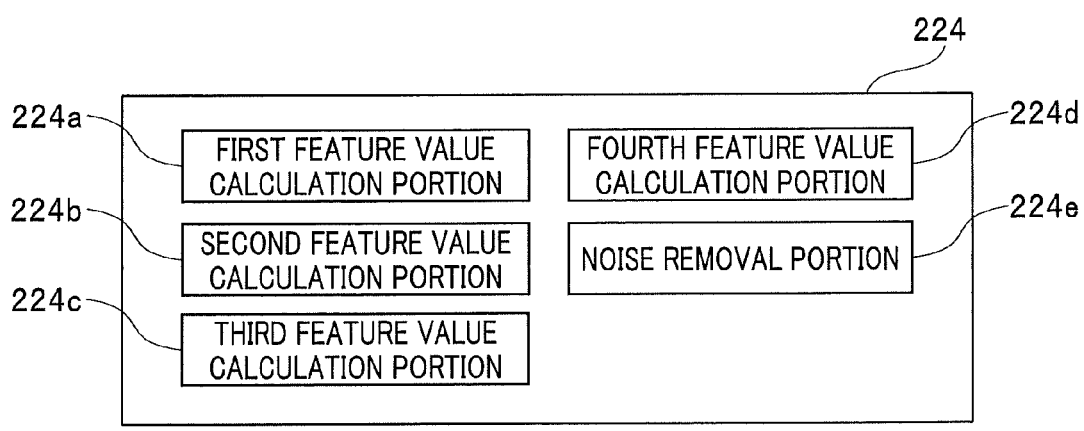
FIG. 3 is a diagram showing an example of a configuration of an evaluation value calculation portion of the calculation processing portion according to the present example.

FIG. 3 is a diagram showing an example of a configuration of the evaluation value calculation portion of the calculation processing portion according to the present example.

As shown in FIG. 3, the evaluation value calculation portion 224 of the calculation processing portion 22 is configured to include a first feature value calculation portion 224a, a second feature value calculation portion 224b, a third feature value calculation portion 224c, a fourth feature value calculation portion 224d, and a noise removal portion 224e corresponding to functions which are implemented by execution of a program, software, or the like. Note that the respective functions of the portions of the calculation processing portion 22 will be described later.

Action of the medical system 1 with the above-described configuration will be described.

First, a user powers on the portions of the medical system 1 and then inserts the insertion portion 11 into, for example, a stomach of a subject until the distal end portion 14 reaches an interior of the stomach. Upon the insertion, an image of an object at the interior of the stomach which is illuminated with illuminating light (RGB light) exiting from the distal end portion 14 is picked up by the image pickup portion 17, and an image pickup signal corresponding to the object having undergone the image pickup is outputted to the CCU 8.

The CCU 8 converts the image pickup signal outputted from the image pickup device 15 of the image pickup portion 17 to a video signal by subjecting the image pickup signal to signal processing in the signal processing circuit (not shown) and outputs the video signal to the medical image processing apparatus 3 and the monitor 9. The monitor 9 displays the object having undergone the image pickup by the image pickup portion 17 as an image on the basis of the video signal outputted from the CCU 8.

Figure 4:
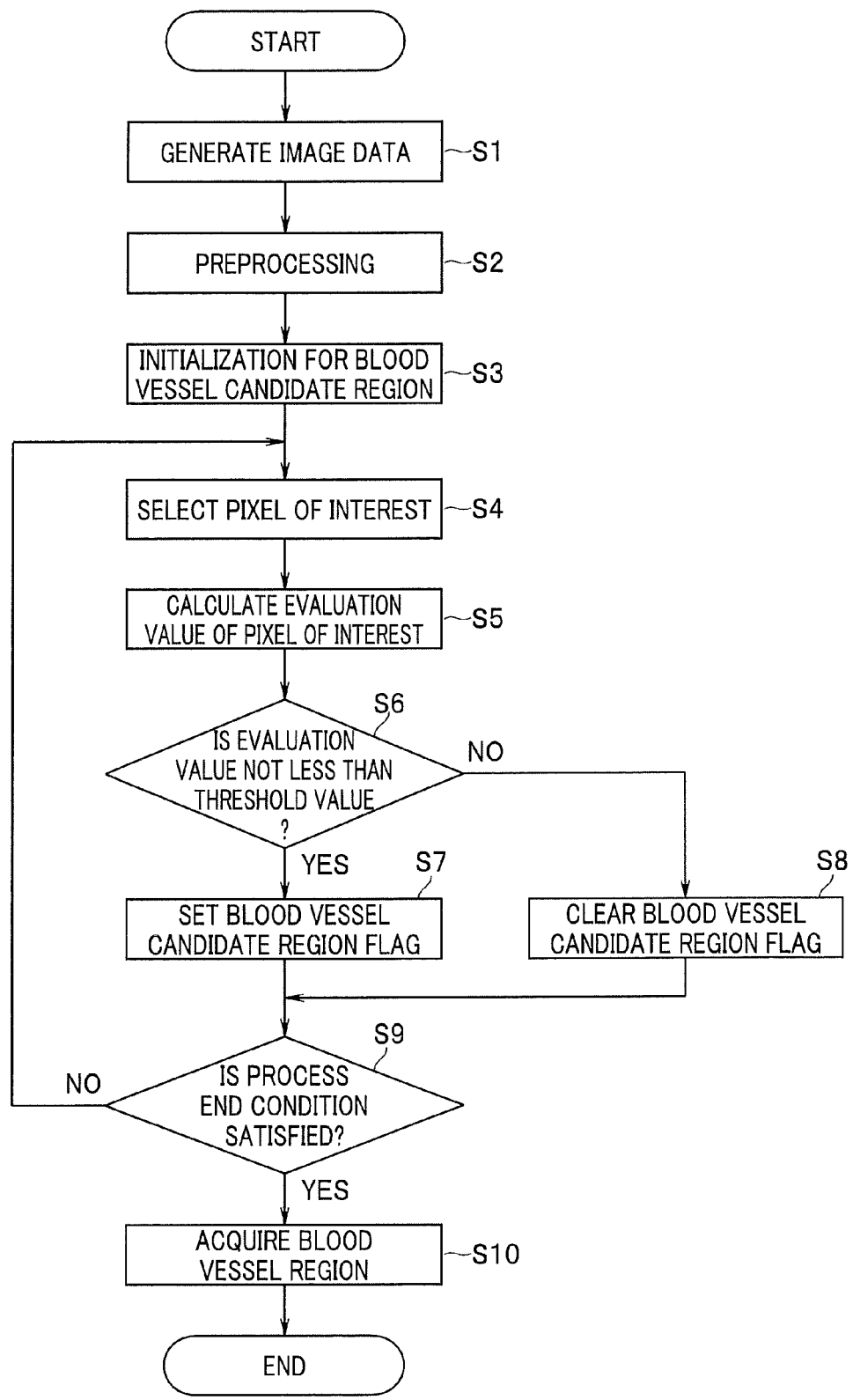
FIG. 4 is a flow chart showing an example of processing to be performed by the medical image processing apparatus according to the present example.

FIG. 4 is a flow chart showing an example of processing to be performed by the medical image processing apparatus according to the present example.

The image input portion 21 of the medical image processing apparatus 3 generates a piece of image data by subjecting an inputted video signal to processing such as A/D conversion and outputs the generated piece of image data to the calculation processing portion 22 (step S1 in FIG. 4). Note that a piece of image data generated in the image input portion 21 according to the present example is assumed to have a size of ISX in length×ISY in width (=640×480) and that an R (red) component, a G (green) component, and a B (blue) component of each pixel are assumed to each have levels of eight bits (256 levels).

The preprocessing portion 221 of the calculation processing portion 22 subjects the piece of image data inputted from the image input portion 21 to preprocessing including degamma processing and noise removal processing using a median filter (step S2 in FIG. 4).

The blood vessel flag setting portion 222 of the calculation processing portion 22 performs initialization for a blood vessel candidate region as a region where a blood vessel may exist in the piece of image data subjected to the preprocessing in the preprocessing portion 221 (step S3 in FIG. 4). More specifically, the blood vessel flag setting portion 222 sets or clears a blood vessel candidate region flag in an initial state for each of pixels included in the piece of image data subjected to the preprocessing by the preprocessing portion 221. In the above-described initialization, for example, the blood vessel flag setting portion 222 according to the present example may uniformly set or clear the respective flags of all of the pixels in the piece of image data, may randomly determine whether to set or clear the flag of each pixel in the piece of image data, or may determine whether to set or clear the flag according to a result of thresholding on a feature value related to color tone or the like of each pixel in the piece of image data.

The pixel selection portion 223 of the calculation processing portion 22 selects a pixel P(i,j) of interest at a pixel position (i,j) among the pixels in the piece of image data (step S4 in FIG. 4). Note that if the size illustrated above (ISX×ISY=640×480) of the piece of image data is taken into account, 0≤i≤639 and 0≤j≤479 hold. The pixel selection portion 223, for example, may select the pixel P(i,j) of interest while scanning the pixels one by one from a pixel at an upper left to a pixel at a lower right of the piece of image data or may randomly select the pixel P(i,j) of interest among the pixels in the piece of image data.

The evaluation value calculation portion 224 of the calculation processing portion 22 calculates, using Equation (1) below, an evaluation value V(i,j) of the pixel P(i,j) of interest selected in step S4 of FIG. 4 (step S5 in FIG. 4).

$$V(i, j) = \frac{w1 \times f_{sv} + w2 \times f_d + w3 \times f_w + w4 \times f_{GR} + w5 \times f_n}{w1 + w2 + w3 + w4 + w5} \quad (1)$$

Note that values of w1, w2, w3, w4, and w5 in a right-hand side of Equation (1) above are assumed to be weighting factors which are set for the terms $f_{sv}$, $f_d$, $f_w$, $f_{GR}$, and $f_n$, respectively. More specifically, the values of w1, w2, w3, w4, and w5 in the right-hand side of Equation (1) above are set to respective values such as 3, 5, 1, 1, and 1.

A specific method for calculating values of $f_{sv}$, $f_d$, $f_w$, $f_{GR}$, and $f_n$ in Equation (1) above and the like will be described.

The first feature value calculation portion 224a of the evaluation value calculation portion 224 calculates the feature value $f_{sv}$ of the pixel P(i,j) of interest selected in step S4 of FIG. 4.

More specifically, the first feature value calculation portion 224a first calculates a value (hereinafter referred to as a G/R value) obtained by dividing a pixel value of a G component by a pixel value of an R component for each pixel in the piece of image data.

After that, the first feature value calculation portion 224a applies each of one-dimensional filters F1, F2, and F3 having the filter factors illustrated below to the G/R value (a piece of color tone information) of the pixel P(i,j) of interest and G/R values (pieces of color tone information) of two sets of a predetermined number of pixels (linearly) continuous in each of a set of left and right directions, a set of upward and downward directions, a set of first diagonal directions (a 45° direction and a 225° direction), and a set of second diagonal directions (a 135° direction and a 315° direction) from the pixel P(i,j) of interest as a center among a result of calculating the G/R values corresponding to pieces of color tone information of each of the pixels in the piece of image data.

$$F1=\{0.182375, 0.32356, 0.1682, -0.3481, -0.652,\\ -0.3481, 0.1682, 0.32356, 0.18238\}$$

$$F2=\{0.19347, 0.28177, 0.24509, -0.0356, -0.4009,\\ -0.5676, -0.4009, -0.0356, 0.24509, 0.28177,\\ 0.19347\}$$

$$F3=\{0.16261, 0.18215, 0.2109, 0.20337, 0.08723,\\ -0.1554, -0.4214, -0.5389, -0.4214, -0.1554,\\ 0.08723, 0.20337, 0.2109, 0.18215, 0.16261\}$$

The above-described one-dimensional filter F1 is a matched filter which is designed so as to be capable of suitably detecting a blood vessel having a width corresponding to five pixels when the one-dimensional filter F1 is applied to a result of calculating G/R values and is configured to have filter factors for nine pixels. That is, the first feature value calculation portion 224a obtains four output values, from which presence or absence of a blood vessel having a width corresponding to five pixels can be judged, by performing a product-sum operation using G/R values of nine pixels, which are composed of the pixel P(i,j) of interest and four pixels continuous in either direction (on either side) from the pixel P(i,j) of interest as the center, and the filter factors of the one-dimensional filter F1 for each of the above-described sets of directions.

The above-described one-dimensional filter F2 is a matched filter which is designed so as to be capable of suitably detecting a blood vessel having a width corresponding to seven pixels when the one-dimensional filter F2 is applied to a result of calculating G/R values and is configured to have filter factors for 11 pixels. That is, the first feature value calculation portion 224a obtains four output values, from which presence or absence of a blood vessel having a width corresponding to seven pixels can be judged, by performing a product-sum operation using G/R values of 11 pixels, which are composed of the pixel P(i,j) of interest and five pixels continuous in either direction (on either side) from the pixel P(i,j) of interest as the center, and the filter factors of the one-dimensional filter F2 for each of the above-described sets of directions.

The above-described one-dimensional filter F3 is a matched filter which is designed so as to be capable of suitably detecting a blood vessel having a width corresponding to nine pixels when the one-dimensional filter F3 is applied to a result of calculating G/R values and is configured to have filter factors for 15 pixels. That is, the first feature value calculation portion 224a obtains four output values, from which presence or absence of a blood vessel having a width corresponding to nine pixels can be judged, by performing a product-sum operation using G/R values of 15 pixels, which are composed of the pixel P(i,j) of interest and seven pixels continuous in either direction (on either side) from the pixel P(i,j) of interest as the center, and the filter factors of the one-dimensional filter F3 for each of the above-described sets of directions.

Hemoglobin in erythrocyte has strong absorption characteristics in a band of G (green) light among bands of wavelengths constituting RGB light. For the reason, a density value of a G component in a region where a blood vessel exists tends to be lower than a density value of a G component in a region where no blood vessel exists in, for example, image data obtained when an object including the blood vessel is irradiated with RGB light. If variation in the density value of the G component based on the tendency is plotted along a cross-sectional direction of the blood vessel, the plot has a convex downward shape as in FIG. 5.

Figure 5:
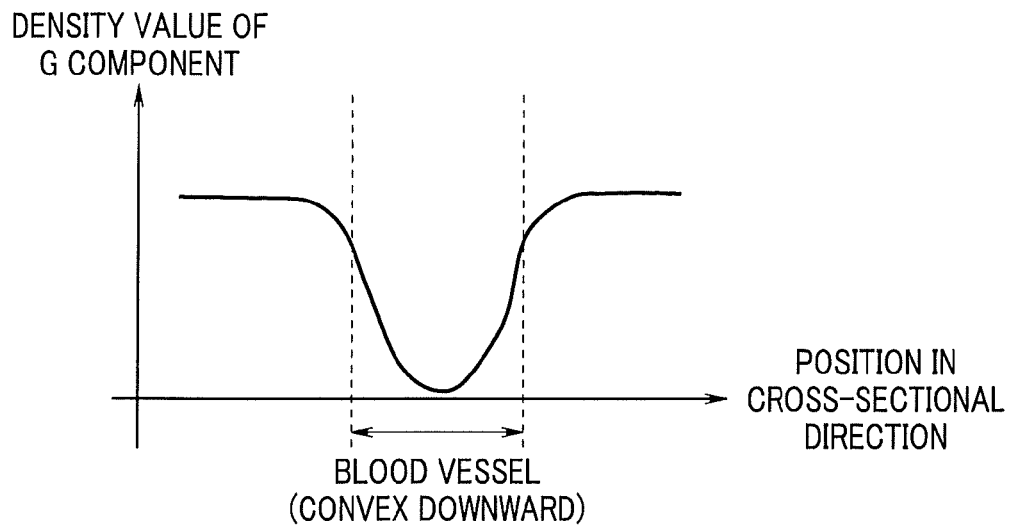
FIG. 5 is a graph for explaining variation in a density value of a green component along a cross-sectional direction of a blood vessel.

That is, each of the one-dimensional filters F1 to F3 is designed to have filter factors that take into account variation in a density value of a G component as illustrated in FIG. 5 and is designed to be capable of detecting a blood vessel having a width corresponding to a predetermined number of pixels substantially without depending on an image pickup condition (e.g., the quantity of illuminating light) when the one-dimensional filter is applied to a result of calculating G/R values. Note that, according to the present example, a piece of color tone information to be used is not limited to a G/R value and that any other value such as a G value (a pixel value of a G component), a G/(R+G+B) value (a value obtained by dividing a pixel value of a G component by the sum of a pixel value of an R component, the pixel value of the G component, and a pixel value of a B component), or a luminance value may be used as a piece of color tone information.

The first feature value calculation portion 224a sets, as the feature value $f_{sv}$ of the pixel P(i,j) of interest, a maximum one among a total of 12 output values obtained by operations using the above-described one-dimensional filters F1, F2, and F3. The first feature value calculation portion 224a also holds a direction orthogonal to a filter application direction when the feature value $f_{sv}$ of the pixel P(i,j) of interest is obtained, as a piece of blood vessel running direction-related direction information of the pixel P(i,j) of interest. The first feature value calculation portion 224a further holds a piece of information on the number of pixels corresponding to a blood vessel width which serves as a filter detection target when the feature value $f_{sv}$ of the pixel P(i,j) of interest is obtained, as a piece of blood vessel width-related width information of the pixel P(i,j) of interest.

Note that the first feature value calculation portion 224a according to the present example is not limited to the above-described configuration which obtains the feature value $f_{sv}$ of the pixel P(i,j) of interest using output values of the one-dimensional filters F1 to F3 and may have, for example, a configuration which obtains the feature value $f_{sv}$ of the pixel P(i,j) of interest using an output value of a Gabor filter or the like which is designed to suit a blood vessel.

The second feature value calculation portion 224b of the evaluation value calculation portion 224 calculates the feature value $f_d$ pertaining to a blood vessel running direction constraint condition on the basis of the piece of blood vessel running direction-related direction information of the pixel P(i,j) of interest selected in step S4 of FIG. 4 and pieces of blood vessel running direction-related direction information of neighboring pixels P(x,y) of the pixel P(i,j) of interest. Note that, for simplicity, a following description will be given in the context of a case where the number of neighboring pixels P(x,y) is eight, i.e., a case where i−1≤x≤i+1 and j−1≤y≤j+1 hold. If x=y=0, values of value_d(x,y) and value_w(x,y) (to be described later) are not calculated.

More specifically, the second feature value calculation portion 224b first calculates a feature value $f_{sv1}$ at the neighboring pixel P(x,y) by applying, for example, any one of the one-dimensional filters F1 to F3 to a result of calculating a G/R value (a piece of color tone information) at the neighboring pixel P(x,y) in each of the set of left and right directions, the set of upward and downward directions, the set of first diagonal directions (the 45° direction and the 225° direction), and the set of second diagonal directions (the 135° direction and the 315° direction) from the neighboring pixel P(x,y) as a center and performing a similar operation to the operation by the first feature value calculation portion 224a. The second feature value calculation portion 224b also holds a direction orthogonal to a filter application direction when the feature value $f_{sv1}$ is obtained, as a piece of blood vessel running direction-related direction information of the neighboring pixel P(x,y).

Note that the filter application directions at the time of calculating the feature value $f_{sv1}$ of the neighboring pixel P(x,y) including the set of left and right directions, the set of upward and downward directions, the set of first diagonal directions (the 45° direction and the 225° direction), and the set of second diagonal directions (the 135° direction and the 315° direction) may be increased or decreased in the process of calculating the feature value $f_d$ by the second feature value calculation portion 224b. The second feature value calculation portion 224b is not limited to the configuration which uses any one of the one-dimensional filters F1 to F3 at the time of calculating the feature value $f_{sv1}$ of the neighboring pixel P(x,y). For example, a band-pass filter which is designed to suit a blood vessel may be used.

After that, the second feature value calculation portion 224b calculates a direction-related constraint value_d(x,y) between the pixel P(i,j) of interest and the neighboring pixel P(x,y) by applying the feature value $f_{sv1}$ at the neighboring pixel P(x,y) to Equation (2) below.

$$\text{value\_}d(x,y) = \text{weight1} \times f_{sv1} \qquad (2)$$

Figure 6:
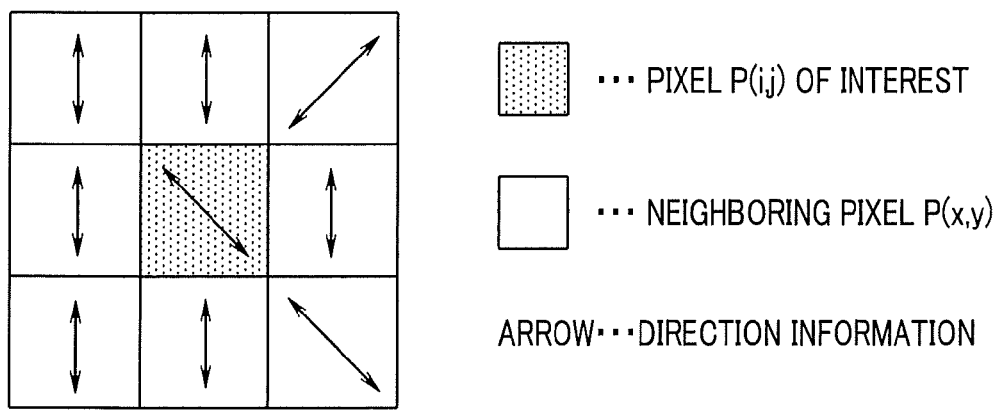
FIG. 6 is a view for explaining processing at the time of calculating a second feature value.

For example, if a blood vessel candidate region flag at the neighboring pixel P(x,y) is on, if the pixel P(i,j) of interest is located in a direction indicated by the piece of direction information of the neighboring pixel P(x,y) from the neighboring pixel P(x,y), and if a direction indicated by the piece of direction information of the pixel P(i,j) of interest and the direction indicated by the piece of direction information of the neighboring pixel P(x,y) are identical to each other, on the basis of the pieces of blood vessel running direction-related direction information of the pixel P(i,j) of interest and the neighboring pixel P(x,y), the second feature value calculation portion 224b sets a value of weight1 in Equation (2) above to 0.2. More specifically, for example, if the blood vessel candidate region flag of the neighboring pixel P(x,y) at a lower right of the pixel P(i,j) of interest in FIG. 6 is on, the above-described conditions are met, and the value of weight1 is set to 0.2. Therefore, if the feature value $f_{sv1}$ of the neighboring pixel P(x,y) at the lower right of the pixel P(i,j) of interest in FIG. 6 is 3.1, the constraint value value_d(x,y) is 0.62.

Additionally, if the blood vessel candidate region flag at the neighboring pixel P(x,y) is on, the pixel P(i,j) of interest is located in the direction indicated by the piece of direction information of the neighboring pixel P(x,y) from the neighboring pixel P(x,y), and the direction indicated by the piece of direction information of the pixel P(i,j) of interest and the direction indicated by the piece of direction information of the neighboring pixel P(x,y) are orthogonal to each other, on the basis of the pieces of blood vessel running direction-related direction information of the pixel P(i,j) of interest and the neighboring pixel P(x,y), the second feature value calculation portion 224b sets the value of weight1 in Equation (2) above to −0.2. More specifically, for example, if the blood vessel candidate region flag of the neighboring pixel P(x,y) at an upper right of the pixel P(i,j) of interest in FIG. 6 is on, the above-described conditions are met, and the value of weight1 is set to −0.2. Therefore, if the feature value $f_{sv1}$ of the neighboring pixel P(x,y) at an upper right of the pixel P(i,j) of interest in FIG. 6 is 3.2, the constraint value value_d(x,y) is −0.64.

Moreover, if neither of the two sets of conditions described above is met on the basis of the pieces of blood vessel running direction-related direction information of the pixel P(i,j) of interest and the neighboring pixel P(x,y), the second feature value calculation portion 224b obtains the constraint value value_d(x,y) of 0 as a calculation result by setting the value of weight1 in Equation (2) above to 0.

Note that the value of weight1 in Equation (2) above is not limited to the above-described values and may be set to other values.

The second feature value calculation portion 224b calculates the feature value $f_d$ of the pixel P(i,j) of interest by performing the operation in Equation (3) below on the basis of a result of calculating the constraint value value_d(x,y).

$$f_d = \frac{\sum_{y=-N}^{N} \sum_{x=-N}^{N} \text{value\_}d(x,y)}{TB} \qquad (3)$$

Note that since the constraint value value_d(x,y) is calculated for each of the eight neighboring pixels P(x,y) of the pixel P(i,j) of interest in the present example, a value of N in a right-hand side of Equation (3) above is set to 1.

Assume that TB in a denominator of the right-hand side of Equation (3) above is a numeric value larger than 0 and is set to a numeric value equal to the number of pixels, for which a result of calculating the constraint value value_d(x,y) that is other than 0 is obtained, among the eight neighboring pixels P(x,y).

For example, if the constraint values value_d(x,y) of each neighboring pixels P(x,y) are all 0 (the value of TB in Equation (3) above is 0) due to, e.g., off state of the blood vessel candidate region flag of each neighboring pixel P(x,y), the second feature value calculation portion 224b sets the value of the feature value $f_d$ of the pixel P(i,j) of interest to 0 without performing the operation in Equation (3) above.

According to the feature value $f_d$ described above, a feature value $f_d$ of a pixel where a blood vessel break due to, e.g., pale color tone is estimated to be occurring is larger than a feature value $f_d$ of another pixel. Therefore, according to the feature value $f_d$ described above, a region where a blood vessel break is estimated to be occurring in a piece of image data can be extracted as a blood vessel candidate region.

The third feature value calculation portion 224c of the evaluation value calculation portion 224 calculates the feature value $f_w$ pertaining to a blood vessel width constraint condition on the basis of the piece of blood vessel width-related width information of the pixel P(i,j) of interest selected in step S4 of FIG. 4 and pieces of blood vessel width-related width information of the neighboring pixels P(x,y) of the pixel P(i,j) of interest.

More specifically, the third feature value calculation portion 224c first calculates a feature value $f_{sv2}$ at the neighboring pixel P(x,y) by applying, for example, the one-dimensional filters F1 to F3 to the result of calculating the G/R value (the piece of color tone information) at the neighboring pixel P(x,y) in each of the set of left and right directions, the set of upward and downward directions, the set of first diagonal directions (the 45° direction and the 225° direction), and the set of second diagonal directions (the 135° direction and the 315° direction) from the neighboring pixel P(x,y) as the center and performing a similar operation to the operation by the first feature value calculation portion 224a. The third feature value calculation portion 224c also holds a piece of information on the number of pixels corresponding to a blood vessel width which serves as a filter detection target when the feature value $f_{sv2}$ is obtained, as the piece of blood vessel width-related width information of the neighboring pixel P(x,y).

Note that the third feature value calculation portion 224c is not limited to the configuration which uses the one-dimensional filters F1 to F3 at the time of calculating the feature value $f_{sv2}$ at the neighboring pixel P(x,y). A plurality of band-pass filters arranged for the respective numbers of pixels corresponding to blood vessel widths that serve as detection targets may be used.

After that, the third feature value calculation portion 224c calculates a width-related constraint value_w(x,y) between the pixel P(i,j) of interest and the neighboring pixel P(x,y) by applying the feature value $f_{sv2}$ at the neighboring pixel P(x,y) to Equation (4) below.

$$\text{value\_}w(x,y) = \text{weight2} \times f_{sv2} \qquad (4)$$

For example, if the blood vessel candidate region flag at the neighboring pixel P(x,y) is on, and if an absolute value of a subtraction result obtained by subtracting the number of pixels corresponding to a blood vessel width included in the piece of width information of the neighboring pixel P(x,y) from the number of pixels corresponding to a blood vessel width included in the piece of width information of the pixel P(i,j) of interest is larger than two, on the basis of the pieces of blood vessel width-related width information of the pixel P(i,j) of interest and the neighboring pixel P(x,y), the third feature value calculation portion 224c sets a value of weight2 in Equation (4) above to −0.2.

If the above-described conditions are not met on the basis of the pieces of blood vessel width-related width information of the pixel P(i,j) of interest and the neighboring pixel P(x,y), the third feature value calculation portion 224c obtains the constraint value value_w(x,y) of 0 as a calculation result by setting the value of weight2 to 0.

Note that the value of weight2 in Equation (4) above is not limited to the above-described values and may be set to other values.

The third feature value calculation portion 224c calculates the feature value $f_w$ of the pixel P(i,j) of interest by performing the operation in Equation (5) below on the basis of a result of calculating the constraint value value_w(x,y).

$$f_w = \frac{\sum_{y=-N}^{N} \sum_{x=-N}^{N} \text{value\_}w(x, y)}{TC} \qquad (5)$$

Note that since the constraint value value_w(x,y) is calculated for each of the eight neighboring pixels P(x,y) of the pixel P(i,j) of interest in the present example, a value of N in a right-hand side of Equation (5) above is set to 1.

Assume that TC in a denominator of the right-hand side of Equation (5) above is a numeric value larger than 0 and is set to a numeric value equal to the number of pixels, for which a result of calculating the constraint value value_w(x,y) that is other than 0 is obtained, among the eight neighboring pixels P(x,y).

For example, if the constraint values value_w(x,y) of each neighboring pixels P(x,y) are all 0 (the value of TC in Equation (5) above is 0) due to, e.g., off state of the blood vessel candidate region flag of each neighboring pixel P(x,y), the third feature value calculation portion 224c sets the value of feature value $f_w$ of the pixel P(i,j) of interest to 0 without performing the operation in Equation (5) above.

According to the feature value $f_w$ described above, a feature value $f_w$ of a pixel where unnatural variation in blood vessel width is estimated to be occurring is smaller than a feature value $f_w$ of another pixel. For the reason, according to the feature value $f_w$ described above, a region where unnatural variation in blood vessel width is estimated to be occurring in a piece of image data can be eliminated from blood vessel candidate regions.

The fourth feature value calculation portion 224d of the evaluation value calculation portion 224 calculates the feature value $f_{GR}$ pertaining to a color tone constraint condition on the basis of a piece of color tone information indicating correlation among color tone of the pixel P(i,j) of interest selected in step S4 of FIG. 4 and color tones of surrounding pixels of the pixel P(i,j) of interest.

More specifically, the fourth feature value calculation portion 224d calculates G/R values (pieces of color tone information) of all pixels included in a rectangular region of a size of 51×51 with the pixel P(i,j) of interest at a center and further calculates an average value GRAvg(i,j) of the G/R values.

Note that the region used to calculate the average value GRAvg(i,j) is not limited to a rectangular region of a size of 51×51 and may be a region of any other size and/or any other shape.

The fourth feature value calculation portion 224d may extract only a group of pixels where a blood vessel is highly likely to actually exist from a predetermined region in the piece of image data and calculate the average value GRAvg(i,j). More specifically, the fourth feature value calculation portion 224d may extract a group of pixels where the value of the feature value $f_{sv}$ is not less than a predetermined value from a rectangular region of a size of 51×51 on the basis of, for example, an operation result from the first feature value calculation portion 224a and calculate the average value GRAvg(i,j) on the basis of G/R values of each of pixels belonging to the extracted group of pixels.

The fourth feature value calculation portion 224d calculates the feature value $f_{GR}$ by applying a result of calculating a G/R value GR(i,j) of the pixel P(i,j) of interest and the average value GRAvg(i,j) to Equation (6) below.

$$f_{GR} = (GRAvg(i,j)/GR(i,j) - 1.0) \times \text{weight3} \qquad (6)$$

Note that weight3 in Equation (6) above is, for example, a constant which is set to an arbitrary numeric value such as 10.0.

The fourth feature value calculation portion 224d may calculate the feature value $f_{GR}$ by applying a value obtained by adding or subtracting standard deviation to or from the average value GRAvg(i,j) to Equation (6) above instead of the average value GRAvg(i,j).

According to the feature value $f_{GR}$ described above, a value of the feature value $f_{GR}$ of a pixel where a blood vessel is highly likely to actually exist is positive while a value of the feature value $f_{GR}$ of a pixel where a blood vessel is unlikely to actually exist is negative. For the reason, according to the feature value $f_{GR}$ described above, a region where a blood vessel is estimated to branch off or blood vessels are estimated to intersect in a piece of image data can be extracted as a blood vessel candidate region.

The noise removal portion 224e of the evaluation value calculation portion 224 judges whether a structure of a local region including the pixel P(i,j) of interest selected in step S4 of FIG. 4 results from noise (whether the structure is an isolated point) and calculates the correction value $f_n$ for correcting the evaluation value V(i,j) on the basis of a result of the judgment.

More specifically, if size of the structure resulting from noise (the isolated point) is less than M×M pixels, the noise removal portion 224e counts the number Cs of pixels having respective set blood vessel candidate flags in a (M+2)×(M+2) rectangular region including the pixel P(i,j) of interest and the number Ct of pixels having respective set blood vessel candidate flags in a (M+4)×(M+4) rectangular region including the pixel P(i,j) of interest.

If Cs=Ct, the noise removal portion 224e judges that the structure of a local region including the pixel P(i,j) of interest results from noise and calculates the correction value $f_n$ of the pixel P(i,j) of interest by multiplying the feature value $f_{sv}$ obtained as an operation result from the first feature value calculation portion 224a by the constant weight4 set to an arbitrary numeric value such as −10.0. On the other hand, if Cs≠Ct, the noise removal portion 224e judges that the structure of the local region including the pixel P(i,j) of interest is not a structure resulting from noise and sets the correction value $f_n$ of the pixel P(i,j) of interest to 0.

In a case where a current processing status is far apart from a process end condition in step S9 of FIG. 4 (to be described later), reliability of on/off status of each blood vessel candidate region flag is considered to be low. In view of the circumstances, the noise removal portion 224e may change weight of the correction value $f_n$ on the basis of correlation between the current processing status and the process end condition in step S9 of FIG. 4.

More specifically, for example, if the process end condition in step S9 of FIG. 4 is defined by the number of times of processing, and Cs=Ct, the noise removal portion 224e may calculate the correction value $f_n$ by acquiring a value of weight_num by dividing the number of times processing having been performed thus far by the number of times required to end processing and applying the obtained value of weight_num to Equation (7) below.

$$f_n = -\text{weight4} \times f_{sv} \times \text{weight\_num} \quad (7)$$

The evaluation value calculation portion 224 of the calculation processing portion 22 calculates the evaluation value V(i,j) of the pixel P(i,j) of interest selected in step S4 of FIG. 4 by applying values of $f_{sv}$, $f_d$, $f_w$, $f_{GR}$, and $f_n$ obtained by the above-described processing to Equation (1) above.

Note that the evaluation value calculation portion 224 of the calculation processing portion 22 is not limited to the configuration which applies the values of $f_{sv}$, $f_d$, $f_w$, $f_{GR}$, and $f_n$ to a numerator in Equation (1) above at the time of calculating the evaluation value V(i,j) of the pixel P(i,j) of interest using Equation (1) above. For example, an operation may be performed by selecting, as a value (values) to be applied to the numerator in Equation (1) above, one or more from among the above-described values. Alternatively, the operation may be performed by adding a term other than the above-described values to the numerator in Equation (1) above (note that since the evaluation value V(i,j) cannot be calculated using the correction value $f_n$ alone due to nature of the correction value $f_n$, the correction value $f_n$ needs to be applied to Equation (1) above together with other values).

The evaluation value judgment portion 225 of the calculation processing portion 22 judges whether the evaluation value V(i,j) calculated in step S5 of FIG. 4 is not less than a threshold value Thre (step S6 in FIG. 4).

If a judgment result showing that the evaluation value V(i,j) is not less than the threshold value Thre, i.e., a judgment result showing that the pixel P(i,j) of interest is a pixel constituting a blood vessel is obtained from the evaluation value judgment portion 225, the blood vessel flag setting portion 222 sets the blood vessel candidate region flag of the pixel P(i,j) of interest (updates the blood vessel candidate region flag to be set) (step S7 in FIG. 4). On the other hand, if a judgment result showing that the evaluation value V(i,j) is less than the threshold value Thre, i.e., a judgment result showing that the pixel P(i,j) of interest is not a pixel constituting a blood vessel is obtained from the evaluation value judgment portion 225, the blood vessel flag setting portion 222 clears the blood vessel candidate region flag of the pixel P(i,j) of interest (updates the blood vessel candidate region flag to be cleared) (step S8 in FIG. 4).

The process end condition judgment portion 226 judges whether the current processing status satisfies the preset process end condition (step S9 in FIG. 4). More specifically, the process end condition judgment portion 226 judges, for example, whether the processes in step S4 to step S8 of FIG. 4 are performed 10 times for each pixel in the piece of image data or whether the number of times the on/off status of the blood vessel candidate region flag at each pixel in the piece of image data is changed (frequency of updates) is less than a predetermined threshold value.

If a judgment result showing that the current processing status does not satisfy the preset process end condition is obtained from the process end condition judgment portion 226, the calculation processing portion 22 performs the processes in step S4 to step S9 of FIG. 4 again in the pixel selection portion 223, the evaluation value calculation portion 224, the evaluation value judgment portion 225, and the process end condition judgment portion 226. On the other hand, if a judgment result showing that the current processing status satisfies the preset process end condition is obtained from the process end condition judgment portion 226, the calculation processing portion 22 detects, as a blood vessel region where a blood vessel can be regarded to actually exist, a region composed of pixels having set blood vessel candidate region flags at a point in time when the judgment result is obtained (step S10 in FIG. 4).

The display processing portion 28 performs coloring or the like on a group of pixels corresponding to a blood vessel region detected by the series of processes in FIG. 4 among the pixels included in the piece of image data inputted from the image input portion 21. With the operation, the display processing portion 28 generates and outputs image signals for displaying an image in which the group of pixels corresponding to the blood vessel region are visualized on the monitor 4.

According to the present embodiment described above, among pixels included in a piece of image data obtained through pickup of an image of a living tissue inside a body cavity, ones with high evaluation values V(i,j) can be detected as a blood vessel region. For the reason, according to the present example, a blood vessel included in an image can be detected with high accuracy.

Note that the example described above is not limited to detection of a blood vessel and may be widely applied to, for example, detection of a tissue having a linear structure, such as a large intestine pit or an epithelial structure. Note that, for example, if the processing according to the present example is applied to a piece of image data obtained by picking up an image of a large intestine pit stained with gentian violet, it is necessary to appropriately change a value to be used as a piece of color tone information, a judgment condition, and the like while taking into account that variation in a density value of a G component along a cross-sectional direction of a blood vessel has not a convex downward shape as illustrated in FIG. 5 but a convex upward shape.

Additionally, the above-described example is not limited to application to a piece of image data obtained through image pickup by an endoscope and can also be used to, for example, detect a line segment such as a blood vessel included in a piece of image data obtained by picking up an image of a fundus.

The present invention is not limited to the above example. Of course, various changes and applications may be made without departing from scope and spirit of the invention.

What is claimed is:

1. A medical image processing apparatus for detecting a region where a linear structure exists from a piece of image information that is composed of a plurality of pixels and is obtained by picking up an image of a living tissue, the medical image processing apparatus including:
    a selection portion that selects a pixel of interest from the piece of image information;
    a first feature value calculation portion that calculates a first feature value of the pixel of interest which is calculated by a first calculation method for extracting a first feature from the plurality of pixels, on the basis of a piece of color tone information of the pixel of interest and pieces of color tone information of surrounding pixels;
    a second feature value calculation portion that calculates a second feature value of the pixel of interest which is calculated by a second calculation method different from the first calculation method for extracting a second feature different from the first feature from the plurality of pixels, on the basis of the piece of color tone information of the pixel of interest and pieces of color tone information of surrounding pixels;
    an evaluation value calculation portion that calculates an evaluation value of the pixel of interest serving as a value used to judge on the basis of the first feature value and the second feature value whether the pixel of interest is a pixel corresponding to a linear structure; and
    an evaluation value judgment portion that judges whether the pixel of interest is a pixel constituting a linear structure, on the basis of the evaluation value calculated by the evaluation value calculation portion.

2. The medical image processing apparatus according to claim 1, wherein
    the first feature value calculation portion includes a first feature information holding portion that holds a piece of feature information of the pixel of interest obtained at the time of calculating the first feature value, and
    the second feature value calculation portion calculates the second feature value using the piece of feature information of the pixel of interest that is held by the first feature information holding portion.

3. The medical image processing apparatus according to claim 2, wherein
    the second feature value calculation portion
    includes a second feature information holding portion that holds pieces of feature information of each of pixels in a neighboring region of the pixel of interest and
    calculates the second feature value on the basis of the piece of feature information of the pixel of interest and the pieces of feature information of the each of the pixels in the neighboring region of the pixel of interest.

4. The medical image processing apparatus according to claim 3, wherein
    the first feature value calculation portion includes
    a first color tone information acquisition portion that acquires the piece of color tone information for each of the pixel of interest and a plurality of pixels continuous with the pixel of interest and
    a first filter application portion that applies a filter which is designed to suit the linear structure to the pieces of color tone information acquired at the pixel of interest and the plurality of pixels and
    calculates the first feature value of the pixel of interest on the basis of a result of applying the filter and holds the piece of feature information of the pixel of interest in the first feature information holding portion.

5. The medical image processing apparatus according to claim 4, wherein
    the second feature value calculation portion includes
    a second color tone information acquisition portion that acquires the piece of color tone information of each of the pixels in the neighboring region of the pixel of interest,
    a second filter application portion that applies a filter which is designed to suit the linear structure to the piece of color tone information acquired at each of the pixels in the neighboring region, and
    the second feature information holding portion that holds pieces of feature information of each of the pixels in the neighboring region of the pixel of interest based on an application result from the second filter application portion.

6. The medical image processing apparatus according to claim 5, wherein
    the first feature information holding portion holds, as the piece of feature information of the pixel of interest, a piece of information related to a running direction of the linear structure at the pixel of interest which is based on a direction in which the filter is applied by the first filter application portion,
    the second feature information holding portion holds, as the piece of feature information at each pixel in the neighboring region of the pixel of interest, a piece of information related to a running direction of the linear structure at each pixel in the neighboring region of the pixel of interest that is based on a direction in which the filter is applied by the second filter application portion, and
    the second feature value calculation portion calculates, as the second feature value, a feature value of the pixel of interest pertaining to a constraint condition for a running direction of the linear structure from the piece of information related to the running direction of the linear structure at the pixel of interest and the piece of information related to the running direction of the linear structure at each pixel in the neighboring region of the pixel of interest.

7. The medical image processing apparatus according to claim 5, wherein
    the first feature information holding portion holds, as the piece of feature information of the pixel of interest, a piece of information related to width of the linear structure at the pixel of interest that is based on design of the filter by the first filter application portion,
    the second feature information holding portion holds, as the piece of feature information at each pixel in the neighboring region of the pixel of interest, a piece of information related to width of the linear structure at each pixel in the neighboring region of the pixel of interest that is based on design of the filter by the second filter application portion, and
    the second feature value calculation portion calculates, as the second feature value, a feature value of the pixel of interest pertaining to a constraint condition for width of the linear structure from the piece of information related to width of the linear structure at the pixel of interest and the piece of information related to width of the linear structure at each pixel in the neighboring region of the pixel of interest.

8. The medical image processing apparatus according to claim 1, wherein the first feature value calculation portion includes a color tone information acquisition portion that acquires the piece of color tone information for each of pixels in a local region including the pixel of interest and calculates a feature value of the pixel of interest pertaining to a constraint condition for color tone of the linear structure, on the basis of the pieces of color tone information acquired at each of the pixels in the local region.

9. The medical image processing apparatus according to claim 1, further including a process end condition judgment portion that judges whether a predetermined process end condition is satisfied, wherein processing by the selection portion, the first feature value calculation portion, the second feature value calculation portion, the evaluation value calculation portion, and the evaluation value judgment portion is repeatedly performed until the predetermined condition is satisfied.

10. A method for operating a medical image processing apparatus for detecting pixels in a region where a linear structure exists from a piece of image information that is composed of a plurality of pixels and is obtained by picking up an image of a living tissue, the method for operating the medical image processing apparatus, including:

a selection step of selecting, by a selection portion of the medical image processing apparatus, a pixel of interest from the piece of image information;

a first feature value calculation step of calculating, by a first feature value calculation portion of the medical image processing apparatus, a first feature value of the pixel of interest that is calculated by a first calculation method for extracting a first feature from the plurality of pixels, on the basis of a piece of color tone information of the pixel of interest selected by the selection portion and pieces of color tone information of surrounding pixels;

a second feature value calculation step of calculating, by a second feature value calculation portion of the medical image processing apparatus, a second feature value of the pixel of interest that is calculated by a second calculation method different from the first calculation method for extracting a second feature different from the first feature from the plurality of pixels, on the basis of the piece of color tone information of the pixel of interest selected by the selection portion and pieces of color tone information of surrounding pixels;

an evaluation value calculation step of calculating, by an evaluation value calculation portion of the medical image processing apparatus, an evaluation value of the pixel of interest serving as a value used to judge, on the basis of the first feature value calculated by the first feature value calculation portion and the second feature value calculated by the second feature value calculation portion, whether the pixel of interest is a pixel corresponding to a linear structure; and an evaluation value judgment step of judging, by an evaluation value judgment portion of the medical image processing apparatus, whether the pixel of interest is a pixel constituting a linear structure, on the basis of the evaluation value calculated by the evaluation value calculation portion.

11. The method for operating the medical image processing apparatus according to claim 10, wherein the first feature value calculation step includes a first feature information holding step of holding a piece of feature information of the pixel of interest obtained at the time that the first feature value calculation portion calculates the first feature value, and the second feature value calculation step comprises calculating the second feature value using the piece of feature information of the pixel of interest that is held in the first feature information holding step.

12. The method for operating the medical image processing apparatus according to claim 11, wherein the second calculation method is a calculation method comprising holding pieces of feature information of each of pixels in a neighboring region of the pixel of interest and calculating the second feature value on the basis of the piece of feature information of the pixel of interest and the pieces of feature information of each of the pixels in the neighboring region of the pixel of interest.

13. The method for operating the medical image processing apparatus according to claim 12, wherein the first calculation method is a method comprising acquiring the piece of color tone information for each of the pixel of interest and a plurality of pixels continuous with the pixel of interest, applying a filter that is designed to suit the linear structure to the pieces of color tone information acquired at the pixel of interest and the plurality of pixels, and calculating the first feature value of the pixel of interest on the basis of a result of applying the filter.

14. The method for operating the medical image processing apparatus according to claim 13, wherein the second calculation method comprises acquiring the piece of color tone information of each of the pixels in the neighboring region of the pixel of interest, applying a filter that is designed to suit the linear structure to the piece of color tone information acquired at each of the pixels in the neighboring region, and holding pieces of feature information of each of the pixels in the neighboring region of the pixel of interest based on a result of applying the filter.

15. The method for operating the medical image processing apparatus according to claim 14, wherein the first feature information holding step comprises holding, as the piece of feature information of the pixel of interest, a piece of information related to a running direction of the linear structure at the pixel of interest that is based on a direction in which the filter used in the first calculation method is applied, the second feature value calculation method comprises holding, as the piece of feature information at each pixel in the neighboring region of the pixel of interest, a piece of information related to a running direction of the linear structure at each pixel in the neighboring region of the pixel of interest that is based on a direction in which the filter used in the second feature value calculation method is applied, and the second feature value calculation step comprises calculating, as the second feature value, a feature value of the pixel of interest pertaining to a constraint condition for a running direction of the linear structure from the piece of information related to the running direction of the linear structure at the pixel of interest and the piece of information related to the running direction of the linear structure at each pixel in the neighboring region of the pixel of interest.

16. The method for operating the medical image processing apparatus according to claim 14, wherein
the first feature information holding step comprises holding, as the piece of feature information of the pixel of interest, a piece of information related to width of the linear structure at the pixel of interest that is based on design of the filter used in the first calculation method,
the second feature value calculation method comprises holding, as the piece of feature information at each pixel in the neighboring region of the pixel of interest, a piece of information related to width of the linear structure at each pixel in the neighboring region of the pixel of interest that is based on design of the filter used in the second feature value calculation method, and
the second feature value calculation step comprises calculating, as the second feature value, a feature value of the pixel of interest pertaining to a constraint condition for width of the linear structure from the piece of information related to width of the linear structure at the pixel of interest and the piece of information related to width of the linear structure at each pixel in the neighboring region of the pixel of interest.

17. The method for operating the medical image processing apparatus according to claim 10, wherein
the first feature value calculation step includes
a color tone information acquisition step of acquiring the piece of color tone information for each of pixels in a local region including the pixel of interest and
comprises calculating a feature value of the pixel of interest pertaining to a constraint condition for color tone of the linear structure, on the basis of the pieces of color tone information acquired at each of the pixels in the local region.

18. The method for operating the medical image processing apparatus according to claim 10, further including
a process end condition judgment step of judging whether a predetermined process end condition is satisfied by a process end condition judgment portion of the medical image processing apparatus, wherein
processing in the selection step, the first feature value calculation step, the second feature value calculation step, the evaluation value calculation step, and the evaluation value judgment step is repeatedly performed by the medical image processing apparatus until the predetermined condition is satisfied.

* * * * *